United States Patent [19]

Seemuth

[11] 4,405,334
[45] Sep. 20, 1983

[54] DIESEL FUEL COMPOSITION
[75] Inventor: Paul D. Seemuth, Oak Park, Mich.
[73] Assignee: Ethyl Corporation, Richmond, Va.
[21] Appl. No.: 424,053
[22] Filed: Sep. 27, 1982
[51] Int. Cl.$^3$ .............................................. C01L 1/22
[52] U.S. Cl. ......................................... 44/53; 44/56; 44/57; 44/63; 546/242
[58] Field of Search .......................... 44/53, 56, 57, 63; 546/242

[56] References Cited

U.S. PATENT DOCUMENTS 3,551,432 12/1970 Wendler et al. .................... 546/242
3,845,062 10/1974 Henecka et al. .................... 546/242

FOREIGN PATENT DOCUMENTS 627452 9/1961 Canada ............................... 546/242

*Primary Examiner*—Charles F. Warren
*Assistant Examiner*—Y. Harris-Smith
*Attorney, Agent, or Firm*—Donald L. Johnson; John F. Sieberth; Joseph D. Odenweller

[57] ABSTRACT

The cetane rating of diesel fuel, both hydrocarbon and alcohol, is increased by adding a 1-alkylpiperidinol nitrate ester, e.g. 1-methyl-3 or 4-piperidinol nitrate.

13 Claims, No Drawings

DIESEL FUEL COMPOSITION

BACKGROUND

Diesel engines operate by compression ignition. They have compression ratios in the range of 14:1 to 17:1 or higher and for that reason obtain more useful work from a given amount of fuel compared to an Otto cycle engine. Historically, diesel engines have been operated on a petroleum-derived liquid hydrocarbon fuel boiling in the range of about 300°-750° F. Recently, because of dwindling petroleum reserves, alcohol and alcohol-hydrocarbon blends have been studied for use as diesel fuel.

One major factor in diesel fuel quality is cetane number. Cetane number is related to ignition delay after the fuel is injected into the combustion chamber. If ignition delays too long, the amount of fuel in the chamber increases and upon ignition results in a rough running engine and increased smoke. A short ignition delay results in smooth engine operation and decreases smoke. Commercial petroleum diesel fuels generally have a cetane number of about 40-55. Alcohols have a much lower cetane value and require the addition of a cetane improver for successful engine operation.

Through the years, many types of additives have been used to raise the cetane number of diesel fuel. These include peroxides, nitrites, nitrates, nitrosocarbamates, and the like. Alkyl nirates such as amyl nitrate, hexyl nitrate and mixed octyl nitrates have been used commercially with good results.

SUMMARY

It has now been discovered that certain novel 1-alkyl piperidinol nitrates are very effective in increasing the cetane number of diesel fuel.

DESCRIPTION OF THE PREFERRED EMBODIMENTS

A preferred embodiment of the invention is liquid fuel adapted for use in a diesel engine, said fuel being selected from the group consisting of liquid hydrocarbons of the diesel boiling range, alcohols and mixtures thereof, said fuel containing a cetane number increasing amount of a 1-alkylpiperidinol nirate.

The 1-alkylpiperidinol nitrate may be substituted in the heterocyclic ring by groups in addition to the nitrate group. For example, the ring substituent can include alkyl (e.g. methyl, ethyl, n-propyl, dodecyl and the like), aryl (e.g. phenyl, tolyl and the like), halo (e.g. chloro, bromo and the like), alkoxy (e.g. methoxy, ethoxy, propoxy, and the like), aralkyl (e.g. benzyl, α-methylbenzyl and the like), cycloalkyl (e.g. cyclopentyl, cyclohexyl, and the like) and alkenyl (e.g. allyl, octenyl, dodecenyl and the like.

The 1-alkyl or N-alkyl group can be any alkyl such as those containing 1-20 carbon atoms. These include methyl, ethyl, n-propyl, isobutyl, n-hexyl, 2-ethylhexyl, octadecyl, eicosyl, and the like. More preferably the 1-alkyl group is a lower alkyl containing about 1-8 carbon atoms, still more preferably about 1-4 carbon atoms.

The nitrate ester group is preferably in the 3- or 4-positions. In other words, highly preferred embodiments are 1-alkyl-3-piperidinol nitrate and 1-alkyl-4-piperidinol nitrate. Most preferably, the 1-alkyl group is methyl such that the most preferred additives are 1-methyl-3-piperidinol nitrate and 1-methyl-4-piperidinol nitrate, which are believed to be novel compounds. They have the structure

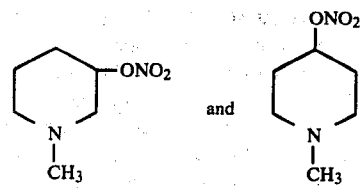

The amount of cetane improver added depends on the type of fuel being used, the initial cetane value, and the amount of cetane number increase desired. Alcohol fuels such as methanol, ethanol, isopropanol, isobutanol, hexanol, and the like, have very low cetane values and large amounts of cetane improvers are required. A useful range in which to operate is about 5-25 weight percent cetane improver.

Blends of alcohol and petroleum-derived diesel fuel have higher cetane values and require less cetane improver. A useful range is about 0.5-10 weight percent.

Petroleum-derived distillate fuels in the diesel boiling range require only small amounts of cetane improver to achieve a significant increase in cetane number. Such fuels without any cetane improver generally have cetane numbers in the range of about 25-60. Cetane numbers in the range of 25-35 are considered low and those in the range of 50-60 are considered top grade diesel fuels. Diesel fuels in the 35-50 mid-range are most common. An object of the invention is to upgrade the low cetane number fuels at least into the mid-range and to increase the cetane value of the mid-range fuels into the upper portion of the mid-range (e.g. 45-50) or even into the premium range above 50. It has been found that highly beneficial results can be achieved using as little as 0.05 weight percent of the present additive. Accordingly, a useful concentration range in petroleum derived diesel fuel is about 0.01-5 weight percent and more preferably about 0.05-0.5 weight percent.

The cetane number improving additives can be made by reacting the appropriate 1-alkyl piperidinol with mixed nitric-sulfuric acid at low temperatures, e.g. −15° to 0° C.

EXAMPLE 1

In a reaction vessel was placed 27 g. (0.3 mole) 70 percent nitric acid. This was stirred and 86.5 g 98 percent sulfuric acid was added slowly at −16° to −10° C. Then 0.2 g. of urea was added. To this was added dropwise 23.5 g. (0.2 mole) 4-hydroxy-N-methyl piperidine also named 1-methyl-4-piperidinol over a 48 minute period at −9° to −12° C. The resulting mixture was poured into an ice-water mixture. The acidic aqueous solution was neutralized with sodium carbonate (pH 9.0) and extracted twice with diethyl ether. The extracts were combined and dried over anhydrous Na$_2$SO$_4$. The ether was distilled out under vacuum (30° C. per 30 mm Hg absol.) leaving 11.78 g of yellow oil. Infrared confirmed it as 1-methyl-4-piperidinol nitrate.

The aqueous phase was extracted again with three portions of ethyl acetate. The extract was dried as before and the ethyl acetate distilled out under vacuum leaving 11.47 g. of product. This was identified by infrared to be the same as the ether extracted product. Both products were combined.

EXAMPLE 2

In a reaction vessel was placed 85.6 g. conc. sulfuric acid. This was stirred at −20° C. and 19.1 ml(0.3 mole) conc. nitric (70 percent) was added at −11.6° to −20° C. Then 0.2 g. of urea was added followed by 23.5 g (0.2 mole) 3-hydroxy-N-methyl piperidine at −9 to −12° C. over a 46 min. period. The reaction mixture was poured into an ice-water mixture (150 ml). The aqueous solution was neutralized with sodium carbonate and extracted as in Example 1, first with diethyl ether (3×100 ml) and then with ethyl acetate (2×100 ml plus 1×150 ml). Both extracts were dried over anhydrous sodium sulfate and the solvents were distilled out under vacuum. The ether extract gave 19.49 g of residual liquid which was identified by infrared as 1-methyl-3-piperidinol nitrate. The 1.21 g. residual from the ethyl acetate extract contained nitrate but a strong hydroxyl bond remained so it was discarded.

Other 1-alkylpiperidinol nitrates can be made following the above general procedure by substituting other 1-alkylpiperidinol starting materials.

The cetane increase caused by the present additives was measured in comparison with that caused by a commercial cetane improver, isooctyl nitrate, using a standard cetane engine. The fuel used was a blend of 46 cetane number diesel fuel and 28 cetane number light cycle oil resulting in a 38 cetane number blend diesel fuel. The results at various concentrations are shown in the following table.

| Concentration (wt %) | Isooctyl Nitrate | 1-Methyl-3-piperidinol Nitrate | 1-Methyl-4-piperidinol Nitrate |
|---|---|---|---|
| None | 38 | 38 | 38 |
| 0.05 | 39.3 | 40.46 | 39.44 |
| 0.10 | 40.5 | 42.41 | 40.66 |
| 0.15 | 41.8 | 43.17 | 43.32 |

Other conventional additives may be included in the diesel fuel including antioxidants, pour point depressants, cold filter plugging inhibitors, detergents, rust inhibitors and the like, including other cetane improvers.

I claim:

1. Liquid fuel adapted for use in a diesel engine, said fuel being selected from the group consisting of liquid hydrocarbons of the diesel boiling range, alcohols and mixtures thereof, said fuel containing a cetane number increasing amount of a 1-alkylpiperidinol nitrate.

2. A liquid fuel composition of claim 1 wherein said 1-alkylpiperidinol nitrate is a 1-alkyl-3-piperidinol nitrate.

3. A liquid fuel composition of claim 1 wherein said 1-alkylpiperidinol nitrate is a 1-alkyl-4-piperidinol nitrate.

4. A liquid fuel composition of claim 1 wherein said fuel is a liquid hydrocarbon of the diesel boiling range.

5. A liquid fuel composition of claim 4 wherein said 1-alkylpiperidinol nitrate is a 1-alkyl-3-piperidinol nitrate.

6. A liquid fuel composition of claim 5 wherein said 1-alkyl-3-piperidinol nitrate is 1-methyl-3-piperidinol nitrate.

7. A liquid fuel composition of claim 4 wherein said 1-alkylpiperidinol nitrate is a 1-alkyl-4-piperidinol nitrate.

8. A liquid fuel composition of claim 7 wherein said 1-alkyl-4-piperidinol nitrate is 1-methyl-4-piperidinol nitrate.

9. An additive useful in increasing the cetane number of diesel fuel, said additive being a 1-alkyl piperidinol nitrate.

10. An additive of claim 9 which is a 1-alkyl-3-piperidinol nitrate.

11. An additive of claim 10 which is 1-methyl-3-piperidinol nitrate.

12. An additive of claim 9 which is a 1-alkyl-4-piperidinol nitrate.

13. An additive of claim 12 which is 1-methyl-4-piperidinol nitrate.

* * * * *